(12) United States Patent
Jackson et al.

(10) Patent No.: US 7,893,270 B2
(45) Date of Patent: Feb. 22, 2011

(54) PROCESS FOR THE PRODUCTION OF CYCLIC DIKETONES

(75) Inventors: David Anthony Jackson, Huddersfield (GB); Andrew Edmunds, Basel (CH); Martin Charles Bowden, Huddersfield (GB); Ben Brockbank, Huddersfield (GB)

(73) Assignee: Syngenta Crop Protection, Inc., Greensboro, NC (US)

( * ) Notice: Subject to any disclaimer, the term of this patent is extended or adjusted under 35 U.S.C. 154(b) by 816 days.

(21) Appl. No.: 11/568,077

(22) PCT Filed: Apr. 29, 2005

(86) PCT No.: PCT/EP2005/004680

§ 371 (c)(1),
(2), (4) Date: Sep. 28, 2007

(87) PCT Pub. No.: WO2005/105718

PCT Pub. Date: Nov. 10, 2005

(65) Prior Publication Data

US 2008/0139816 A1    Jun. 12, 2008

(30) Foreign Application Priority Data

Apr. 30, 2004    (CH)    .................... 0766/04

(51) Int. Cl.
*C07D 213/80*    (2006.01)
*C07C 22/04*    (2006.01)

(52) U.S. Cl. ................... 546/322; 560/12; 560/59; 570/190

(58) Field of Classification Search .............. None
See application file for complete search history.

(56) References Cited

U.S. PATENT DOCUMENTS

2002/0016345 A1    2/2002    Edmunds et al.
2002/0165096 A1    11/2002    Schaetzer et al.

FOREIGN PATENT DOCUMENTS

EP    1352901 A2    10/2003

OTHER PUBLICATIONS

Database Beilstein [online]; XP-002339791 Accession No. Rid 4517729: Abstract, 1996.

*Primary Examiner*—Zinna N Davis
(74) *Attorney, Agent, or Firm*—William A. Teoli, Jr.

(57) ABSTRACT

The present invention relates to a process for the preparation of compounds of formula (I), wherein the substituents are as defined in claim 1, by reacting a compound of formula (II), with a bromine or chlorine source to form a compound of formula (III), wherein X is chlorine or bromine; reacting that compound with water to form the compound of formula (IV), converting that compound, using a compound of formula (V), wherein $M^+$ is the hydrogen cation or an alkali metal ion, alkaline earth metal ion or ammonium ion, into the compound of formula (VI), and treating that compound with a cyanide source in the presence of a base.

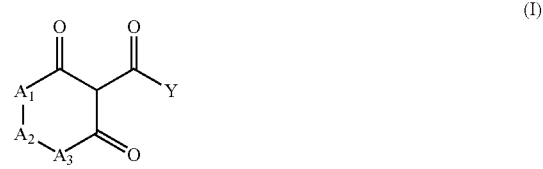

(I)

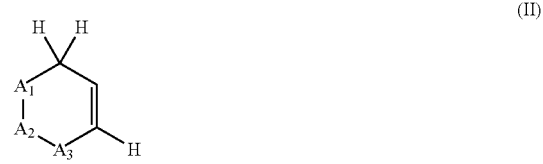

(II)

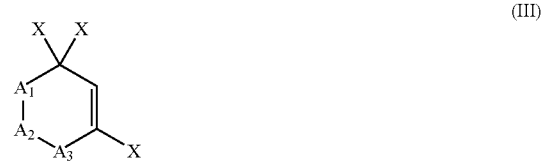

(III)

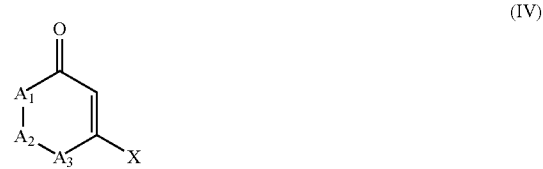

(IV)

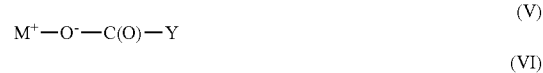

(V)

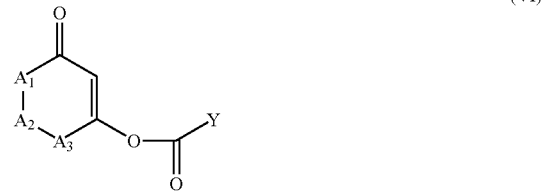

(VI)

1 Claim, No Drawings

PROCESS FOR THE PRODUCTION OF CYCLIC DIKETONES

This application is a 371 of International Application No. PCT/EP2005/004680 filed Apr. 29, 2005, which claims priority to CH 00766/04 filed Apr. 30, 2004, the contents of which are incorporated herein by reference.

The present invention relates to a process for the preparation of cyclic 1,3-diketone derivatives carbonylated in the 2-position.

Processes for the preparation of cyclic 1,3-diketones substituted in the 2-position by an arylcarbonyl group are described, for example, in WO/0015615, WO 00/37437, WO 01/66522 and WO 01/94339. The compounds disclosed therein have herbicidal action.

Those known processes have the disadvantage, however, that certain cyclic 1,3-diketone starting compounds unsubstituted in the 2-position, especially the bicyclic 1,3-diketone starting compounds, are generally not readily accessible and their derivatives can usually be prepared only by means of a plurality of laborious synthesis steps and purification procedures.

Furthermore, in the known processes the isolation of the end products, especially in the case of 2-benzoyl, 2-pyridycarbonyl and 2-heteroarylcarbonyl derivatives, involves a generally multi-step procedure which is highly laborious. The purity and yield of the cyclic 1,3-diketones prepared using the known processes are therefore often unsatisfactory.

The problem of the present invention is accordingly to make available a novel general process for the preparation of monocyclic and bicyclic 1,3-diketone derivatives, especially 2-benzoyl, 2-isonicotinoyl and 2-nicotinoyl derivatives, which makes it possible to prepare such compounds in high yields and good quality with a simple reaction procedure and little outlay without the above-mentioned disadvantages of the known processes.

The present invention accordingly relates to a process for the preparation of compounds of formula I

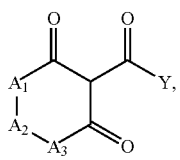

(I)

wherein

Y is an organic substituent which is so selected that the compound of formula I has a pK value of from 1 to 5;

$A_1$ is $CR_1R_2$;

$A_2$ is oxygen, $C(O)$, $SO_2$ or $(CR_3R_4)_n$;

n is 1 or 2;

$A_3$ is $CR_5R_6$;

$R_1$, $R_2$, $R_3$, $R_4$, $R_5$ and $R_6$ are each independently of the others $C_1$-$C_4$alkyl which may be mono-, di- or tri-substituted by $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl or by heteroaryl, it being possible for the phenyl and heteroaryl groups in turn to be mono-, di- or tri-substituted by $C_1$-$C_4$alkoxy, halogen, hydroxy, cyano, hydroxycarbonyl, $C_1$-$C_4$alkoxycarbonyl, $C_1$-$C_4$alkylsulfonyl or by $C_1$-$C_4$haloalkyl, the substituents on the nitrogen in the heterocyclic ring being other than halogen; and/or $R_1$, $R_2$, $R_3$, $R_4$, $R_5$ and $R_6$ are each independently of the others hydrogen, $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl or heteroaryl, it being possible for the phenyl and heteroaryl groups in turn to be mono-, di- or tri-substituted by $C_1$-$C_4$alkoxy, halogen, hydroxy, cyano, hydroxycarbonyl, $C_1$-$C_4$alkoxycarbonyl, $C_1$-$C_4$alkylsulfonyl or by $C_1$-$C_4$haloalkyl, the substituents on the nitrogen in the heterocyclic ring being other than halogen; and/or $R_1$ and $R_2$ together form a 3- to 5-membered carbocyclic ring which may be substituted by $C_1$-$C_4$alkyl and/or interrupted by oxygen, sulfur, $S(O)$, $SO_2$, $OC(O)$, $NR_7$ or by $C(O)$; and/or $R_2$ and $R_4$ together or $R_2$ and $R_5$ together form a $C_1$-$C_3$alkylene chain which may be interrupted by oxygen, sulfur, $SO$, $SO_2$, $OC(O)$, $NR_8$ or by $C(O)$; it being possible for that $C_1$-$C_3$alkylene chain in turn to be substituted by $C_1$-$C_4$alkyl; and $R_7$ and $R_8$ are each independently of the other $C_1$-$C_4$alkyl, $C_1$-$C_4$haloalkyl, $C_1$-$C_4$alkylsulfonyl, $C_1$-$C_4$alkylcarbonyl or $C_1$-$C_4$alkoxycarbonyl; in which process a) a compound of formula II (II)

wherein $A_1$, $A_2$ and $A_3$ are as defined for formula I, is reacted with a bromine or chlorine source to form a compound of formula III (III)

wherein $A_1$, $A_2$ and $A_3$ are as defined for formula I and X is chlorine or bromine;

b) that compound is reacted with water to form the compound of formula IV (IV)

wherein $A_1$, $A_2$ and $A_3$ are as defined for formula I and X is chlorine or bromine;

c) that compound is converted, using a compound of formula V $$M^+\text{-}O^-\text{---}C(O)\text{---}Y, \quad (V)$$

wherein Y is as defined hereinbefore and $M^+$ is the hydrogen cation or an alkali metal ion, alkaline earth metal ion or ammonium ion, into the compound of formula VI

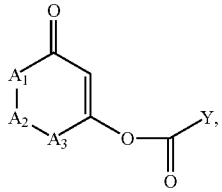
(VI)

wherein $A_1$, $A_2$, $A_3$ and Y are as defined for formula I, and d) then that compound is treated with a cyanide source in the presence of a base.

Y is especially an organic substituent which is so selected that the compound of formula I has a pK value of from 2.5 to 4.5.

The organic substituent Y may be a substituent of any desired structure provided that it remains substantially inert under the reaction conditions of the process according to the invention.

Y is preferably a mono-, di- or tri-substituted phenyl, pyridyl or heteroaryl group, especially a di- or tri-substituted phenyl group or a di-substituted 2-pyridyl or 3-pyridyl group; the substitution pattern of those groups being freely selectable provided that the groups remain substantially inert under the reaction conditions of the process according to the invention. Preference is given to phenyl, 3-pyridyl and heteroaryl groups which carry at least one substituent located, very especially, in the ortho position.

Especially advantageously, it is possible, using the process according to the invention, to prepare compounds of formula I wherein Y is

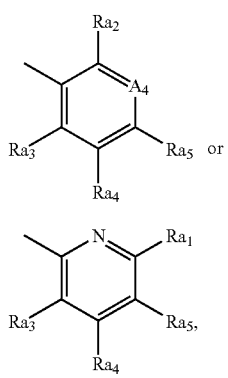

wherein $A_4$ is $CRa_1$ or $=N-(O)_p$;

p is 0 or 1;

$Ra_1$ is hydrogen, $C_1$-$C_6$alkyl, hydroxy, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkynyloxy, $C_1$-$C_4$alkylcarbonyloxy, $C_1$-$C_4$alkylsulfonyloxy, phenylsulfonyloxy, $C_1$-$C_6$alkylthio, $C_1$-$C_6$alkylsulfinyl, $C_1$-$C_6$alkylsulfonyl, $C_1$-$C_6$alkylamino, di($C_1$-$C_6$alkyl)amino, $C_1$-$C_3$alkoxy-$C_1$-$C_3$alkylamino, $C_1$-$C_3$alkoxy-$C_1$-$C_3$alkyl-$N(C_1$-$C_3$alkyl)-, $C_1$-$C_4$alkoxycarbonyl, $C_1$-$C_6$haloalkyl, formyl, cyano, halogen, phenyl or phenoxy, it being possible for the phenyl-containing groups in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro;

or $Ra_1$ is a three- to ten-membered monocyclic or together with $Ra_2$ or $Ra_5$ annellated bicyclic ring system which may be interrupted once or up to three times by heterocyclic substituents selected from oxygen, sulfur, S(O), $SO_2$, $N(Ra_6)$, carbonyl and $C(=NORa_7)$, the ring system, unless it is annellated, being bonded to the carbon atom of the substituent $A_4$ either directly or by way of a $C_1$-$C_4$alkylene, $C_1$-$C_4$alkenylene or $C_2$-$C_4$alkynylene bridge which may be interrupted by oxygen, $-N(C_1$-$C_4$alkyl)-, sulfur, sulfinyl or by sulfonyl, and the ring system may contain not more than 2 oxygen atoms and not more than two sulfur atoms, and the ring system may in turn be mono-, di- or tri-substituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, $C_1$-$C_6$alkylthio, $C_1$-$C_6$haloalkylthio-, $C_3$-$C_6$alkenylthio, $C_3$-$C_6$haloalkenylthio, $C_3$-$C_6$alkynylthio, $C_1$-$C_4$alkoxy-$C_1$-$C_2$alkylthio, $C_1$-$C_4$alkylcarbonyl-$C_1$-$C_2$alkylthio, $C_1$-$C_4$alkoxycarbonyl-$C_1$-$C_2$alkylthio, cyano-$C_1$-$C_4$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_4$alkylaminosulfonyl, di($C_1$-$C_4$alkyl)aminosulfonyl, di($C_1$-$C_4$alkyl)amino, halogen, cyano, nitro, phenyl, benzyloxy and/or by benzylthio, and it being possible for the phenyl-containing groups in turn to be substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or by nitro, and substituents on the nitrogen in the heterocyclic ring are other than halogen;

or $Ra_1$ is the group $-X_5$-$X_7$ or the group $-X_6$-$X_5$-$X_7$; wherein $X_5$ is oxygen, $-O(CO)-$, $-(CO)O-$, $-O(CO)O-$, $-N(C_1$-$C_4$alkyl)-$O-$, $-O-N(C_1$-$C_4$alkyl)-, sulfur, sulfinyl, sulfonyl, $-SO_2N(C_1$-$C_4$alkyl)-, $-N(C_1$-$C_4$alkyl)$SO_2$-, $-N(C_1$-$C_2$alkoxy-$C_1$-$C_2$alkyl)$SO_2$- or $-N(C_1$-$C_4$alkyl)-;

$X_6$ is a $C_1$-$C_6$alkylene, $C_3$-$C_6$alkenylene or $C_3$-$C_6$alkynylene chain which may be mono- or poly-substituted by halogen or by $X_8$, the unsaturated bonds of the chain not being bonded directly to the substituent $X_5$;

$Ra_6$ is hydrogen, $C_1$-$C_4$alkyl, $C_1$-$C_4$alkylthio-$C_1$-$C_4$alkylcarbonyl, $C_1$-$C_4$alkylsulfinyl-$C_1$-$C_4$alkylcarbonyl, $C_1$-$C_4$alkylsulfonyl-$C_1$-$C_4$alkylcarbonyl, $C_1$-$C_4$alkoxycarbonyl, $C_1$-$C_4$alkylcarbonyl, phenylcarbonyl or phenyl, it being possible for the phenyl groups in turn to be substituted by $C_1$-$C_4$alkyl, $C_1$-$C_4$haloalkyl, $C_1$-$C_4$alkoxy, $C_1$-$C_4$haloalkoxy, $C_1$-$C_4$alkylcarbonyl, $C_1$-$C_4$alkoxycarbonyl, $C_1$-$C_4$alkylamino, di($C_1$-$C_4$alkyl)amino, $C_1$-$C_4$alkylthio, $C_1$-$C_4$alkylsulfinyl, $C_1$-$C_4$alkyl-$SO_2$, $C_1$-$C_4$alkyl-$S(O)_2O$, $C_1$-$C_4$haloalkylthio, $C_1$-$C_4$haloalkyl-sulfinyl, $C_1$-$C_4$haloalkyl-$SO_2$, $C_1$-$C_4$haloalkyl-$S(O)_2O$, $C_1$-$C_4$alkyl-$S(O)_2NH$, $C_1$-$C_4$alkyl-$S(O)_2N(C_1$-$C_4$alkyl)-, halogen, nitro or by cyano;

$Ra_7$ is hydrogen, $C_1$-$C_4$alkyl, $C_3$-$C_4$alkenyl, $C_3$-$C_4$alkynyl or benzyl;

$Ra_2$ is hydrogen, $C_1$-$C_6$alkyl, $C_1$-$C_6$haloalkyl, $C_2$-$C_6$alkenyl, $C_2$-$C_6$haloalkenyl; vinyl substituted by $C_1$-$C_2$alkoxycarbonyl or by phenyl; or $C_2$-$C_6$alkynyl, $C_2$-$C_6$haloalkynyl; or ethynyl substituted by trimethylsilyl, hydroxy, $C_1$-$C_6$alkoxy, $C_1$-$C_4$alkoxycarbonyl or by phenyl; $C_3$-$C_6$allenyl, $C_3$-$C_6$cycloalkyl or halo- or $C_1$-$C_3$alkoxymethyl-substituted $C_3$-$C_6$cycloalkyl; or $C_1$-$C_6$alkoxy, $C_3$-$C_6$alkenyloxy, $C_3$-$C_6$alkynyloxy, $C_1$-$C_6$haloalkoxy, $C_3$-$C_6$haloalkenyloxy, cyano-$C_1$-$C_4$alkoxy, $C_1$-$C_4$alkoxy-$C_1$-$C_4$alkoxy, $C_1$-$C_4$alkylthio-$C_1$-$C_4$alkoxy, $C_1$-$C_4$alkylsulfinyl-$C_1$-$C_4$alkoxy, $C_1$-$C_4$alkylsulfonyl-$C_1$-$C_4$alkoxy, $C_1$-$C_4$alkoxycarbonyl-$C_1$-$C_4$alkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_4$alkoxycarbonyl-$C_1$-$C_4$alkylthio, $C_1$-$C_4$alkoxycarbonyl-$C_1$-$C_4$alkylsulfinyl, $C_1$-$C_4$alkoxycarbonyl-$C_1$-$C_4$alkylsulfonyl, $C_1$-$C_6$alkylamino, di($C_1$-$C_6$-alkyl)amino, $C_1$-$C_3$alkoxy-$C_1$-$C_3$alkylamino, $C_1$-$C_3$alkoxy-$C_1$-$C_3$alkyl-N($C_1$-$C_3$alkyl), $C_1$-$C_6$-alkylaminosulfonyl, di($C_1$-$C_6$alkyl)aminosulfonyl, $C_1$-$C_4$alkylsulfonyloxy, $C_1$-$C_4$haloalkylsulfonyloxy, $C_1$-$C_4$alkylsulfonylamino, $C_1$-$C_4$alkylsulfonyl-N($C_1$-$C_4$alkyl), cyano, carbamoyl, $C_1$-$C_4$alkoxycarbonyl, formyl, halogen, rhodano, amino, hydroxy-$C_1$-$C_4$alkyl, $C_1$-$C_4$alkoxy-$C_1$-$C_4$alkyl, $C_1$-$C_4$alkylthio-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl, cyano-$C_1$-$C_4$alkyl, $C_1$-$C_4$alkylcarbonyloxy-$C_1$-$C_4$alkyl, $C_1$-$C_4$alkoxycarbonyl-$C_1$-$C_4$-alkyl, $C_1$-$C_4$alkoxycarbonyloxy-$C_1$-$C_4$alkyl, rhodano-$C_1$-$C_4$alkyl, phenyl-$C_1$-$C_4$alkyl, phenoxy-$C_1$-$C_4$alkyl, benzyloxy-$C_1$-$C_4$alkyl, benzoyloxy-$C_1$-$C_4$alkyl, (2-oxiranyl)-$C_1$-$C_4$alkyl, $C_1$-$C_4$-alkylamino-$C_1$-$C_4$alkyl, di($C_1$-$C_4$alkyl)amino-$C_1$-$C_4$alkyl, $C_1$-$C_{12}$alkylthiocarbonyl-$C_1$-$C_4$alkyl or formyl-$C_1$-$C_4$alkyl, benzylthio, benzylsulfinyl, benzylsulfonyl, benzyloxy, benzyl, phenyl, phenoxy, phenylthio, phenylsulfinyl or phenylsulfonyl; it being possible for the phenyl-containing groups in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro; or $Ra_2$ is a three- to ten-membered monocyclic or annellated bicyclic ring system which may be aromatic, saturated or partially saturated and may contain from 1 to 4 hetero atoms selected from nitrogen, oxygen and sulfur, the ring system being bonded to the group $Q_1$ or $Q_2$ directly or by way of a $C_1$-$C_4$alkylene, $C_1$-$C_4$alkenylene or $C_2$-$C_4$alkynylene bridge which may be interrupted by oxygen, —N($C_1$-$C_4$alkyl)-, sulfur, sulfinyl, sulfonyl or by carbonyl; and each ring system may contain not more than 2 oxygen atoms and not more than two sulfur atoms, and the ring system may in turn be mono-, di- or tri-substituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, hydroxy, mercapto, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_4$alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_4$alkylaminosulfonyl, di($C_1$-$C_4$alkyl)aminosulfonyl, di($C_1$-$C_4$alkyl)amino, halogen, cyano, nitro, phenyl and/or by benzylthio; it being possible for phenyl and benzylthio in turn to be substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or by nitro, and substituents on the nitrogen in the heterocyclic ring are other than halogen; or $Ra_2$ is the group —$X_1$-$X_3$ or the group —$X_2$-$X_1$-$X_3$; wherein $X_1$ is oxygen, —O(CO)—, —(CO)O—, —O(CO)O—, —N($C_1$-$C_4$alkyl)-O—, —O—N($C_1$-$C_4$alkyl)-, thio, sulfinyl, sulfonyl, —$SO_2$N($C_1$-$C_4$alkyl)-, —N($C_1$-$C_4$alkyl)$SO_2$—, —N($C_1$-$C_2$alkoxy-$C_1$-$C_2$alkyl)$SO_2$— or —N($C_1$-$C_4$alkyl)-;

$X_2$ is a $C_1$-$C_6$alkylene, $C_3$-$C_6$alkenylene or $C_3$-$C_6$alkynylene chain which may be mono- or poly-substituted by halogen or by $X_4$, the unsaturated bonds of the chain not being bonded directly to the substituent $X_1$;

$X_3$ and $X_7$ are each independently of the other a $C_1$-$C_8$alkyl, $C_3$-$C_6$alkenyl or $C_3$-$C_6$alkynyl group which may be mono-, di- or tri-substituted by halogen, hydroxy, amino, formyl, nitro, cyano, mercapto, carbamoyl, $C_1$-$C_6$alkoxy, $C_1$-$C_6$alkoxycarbonyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl or halo-substituted $C_3$-$C_6$cycloalkyl; or by $C_3$-$C_6$alkenyloxy, $C_3$-$C_6$alkynyloxy, $C_1$-$C_6$haloalkoxy, $C_3$-$C_6$haloalkenyloxy, cyano-$C_1$-$C_6$-alkoxy, $C_1$-$C_6$alkoxy-$C_1$-$C_6$alkoxy, $C_1$-$C_6$alkoxy-$C_1$-$C_6$alkoxy-$C_1$-$C_6$alkoxy, $C_1$-$C_6$alkylthio-$C_1$-$C_6$alkoxy, $C_1$-$C_6$alkylsulfinyl-$C_1$-$C_6$alkoxy, $C_1$-$C_6$alkylsulfonyl-$C_1$-$C_6$alkoxy, $C_1$-$C_6$alkoxycarbonyl-$C_1$-$C_6$alkoxy, $C_1$-$C_6$alkoxycarbonyl, $C_1$-$C_6$alkylcarbonyl, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl; oxiranyl which may in turn be substituted by $C_1$-$C_6$alkyl; (3-oxetanyl)-oxy which may in turn be substituted by $C_1$-$C_6$alkyl; benzyloxy, benzylthio, benzylsulfinyl, benzylsulfonyl, $C_1$-$C_6$alkylamino, di($C_1$-$C_6$alkyl)amino, $C_1$-$C_4$alkyl-S(O)$_2$O—, di($C_1$-$C_4$alkyl)aminosulfonyl, rhodano, phenyl, phenoxy, phenylthio, phenylsulfinyl or by phenylsulfonyl; and it being possible for the phenyl- or benzyl-containing groups in turn to be substituted by one or more $C_1$-$C_6$alkyl, $C_1$-$C_6$haloalkyl, $C_1$-$C_6$alkoxy, $C_1$-$C_6$haloalkoxy, halogen, cyano, hydroxy or nitro groups; or $X_3$ and $X_7$ are phenyl which may be mono- or poly-substituted by $C_1$-$C_6$alkyl, $C_1$-$C_6$haloalkyl, $C_1$-$C_6$alkoxy, $C_1$-$C_6$haloalkoxy, halogen, cyano, hydroxy or by nitro; or $X_3$ and $X_7$ are each independently of the other $C_3$-$C_6$cycloalkyl, $C_1$-$C_6$alkoxy- or $C_1$-$C_6$alkyl-substituted $C_3$-$C_6$cycloalkyl, 3-oxetanyl or $C_1$-$C_6$alkyl-substituted 3-oxetanyl; or $X_3$ and $X_7$ are each independently of the other a three- to ten-membered monocyclic or annellated bicyclic ring system which may be aromatic, saturated or partially saturated and may contain from 1 to 4 hetero atoms selected from nitrogen, oxygen and sulfur, the ring system being bonded to the substituent $X_1$ or $X_5$ directly or by way of a $C_1$-$C_4$alkylene, $C_2$-$C_4$alkenylene, $C_2$-$C_4$alkynylene, —N($C_1$-$C_4$alkyl)-$C_1$-$C_4$alkylene, —S(O)—$C_1$-$C_4$alkylene or —$SO_2$—$C_1$-$C_4$alkylene group, and each ring system may contain not more than 2 oxygen atoms. and not more than two sulfur atoms, and the ring system may in turn be mono-, di- or tri-substituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, hydroxy, $C_1$-$C_6$haloalkoxy, $C_3$-$C_6$alkenyloxy, $C_3$-$C_6$alkynyloxy, mercapto, $C_1$-$C_6$alkylthio, $C_1$-$C_6$haloalkylthio, $C_3$-$C_6$alkenylthio, $C_3$-$C_6$haloalkenylthio, $C_3$-$C_6$-alkynylthio, $C_1$-$C_3$alkoxy-$C_1$-$C_3$alkylthio, $C_1$-$C_4$alkylcarbonyl-$C_1$-$C_2$alkylthio, $C_1$-$C_4$alkoxycarbonyl-$C_1$-$C_2$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, di($C_1$-$C_2$alkyl)aminosulfonyl, di($C_1$-$C_4$alkyl)amino, $C_1$-$C_6$carbonylamino, halogen, cyano, nitro, phenyl, benzyloxy and/or by benzylthio, it being possible for the phenyl groups in turn to be substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or by nitro, and the substituents on the nitrogen in the heterocyclic ring are other than halogen; and $X_4$ and $X_8$ are each independently of the other hydroxy, $C_1$-$C_6$alkoxy, ($C_3$-$C_6$cycloalkyl)oxy, $C_1$-$C_6$alkoxy-$C_1$-$C_6$alkoxy, $C_1$-$C_6$alkoxy-$C_1$-$C_6$alkoxy-$C_1$-$C_6$alkoxy or $C_1$-$C_6$alkylsulfonyloxy;

$Ra_3$ is hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, amino, $C_1$-$C_6$alkylamino, di($C_1$-$C_6$alkyl)amino, $C_1$-$C_4$alkylsulfonyl-N($C_1$-$C_4$alkyl)-, $C_1$-$C_6$alkylaminosulfonyl, di($C_1$-$C_6$alkyl)aminosulfonyl, cyano, halogen, $C_1$-$C_4$alkoxy-$C_1$-$C_4$alkyl, $C_1$-$C_4$alkylthio-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl, phenyl, phenylthio, phenylsulfinyl, phenylsulfonyl or phenoxy, it being possible for the phenyl groups in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro;

$Ra_4$ is hydrogen, $C_1$-$C_6$alkyl, hydroxy, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkynyloxy, $C_1$-$C_4$alkylcarbonyloxy, $C_1$-$C_4$alkylsulfonyloxy, phenylsulfonyloxy, $C_1$-$C_4$alkylthio, $C_1$-$C_4$alkylsulfinyl, $C_1$-$C_4$alkylsulfonyl, $C_1$-$C_4$alkylamino, di($C_1$-$C_4$alkyl)amino, $C_1$-$C_4$alkoxycarbonyl, $C_1$-$C_4$haloalkyl, formyl, cyano, halogen, phenyl or phenoxy; it being possible for the phenyl-containing groups in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro; or $Ra_4$ is a three- to ten-membered monocyclic or with $Ra_3$ or $Ra_5$ annellated bicyclic ring system which may contain from 1 to 4 hetero atoms selected from nitrogen, oxygen and sulfur, the ring system, unless it is annellated, being bonded to the group $Q_1$ or $Q_2$ either directly or by way of a $C_1$-$C_4$alkylene, $C_1$-$C_4$alkenylene or $C_2$-$C_4$alkynylene bridge which may be interrupted by oxygen, —N($C_1$-$C_4$alkyl)-, sulfur, sulfinyl, sulfonyl or by carbonyl; and the ring system may contain not more than 2 oxygen atoms and not more than two sulfur atoms, and the ring system may in turn may be mono-, di- or tri-substituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_4$alkoxy-$C_1$-$C_2$alkylthio, $C_1$-$C_4$alkylcarbonyl-$C_1$-$C_2$alkylthio, $C_1$-$C_4$alkoxycarbonyl-$C_1$-$C_2$alkylthio, cyano-$C_1$-$C_4$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_4$alkylaminosulfonyl, di($C_1$-$C_4$alkyl)aminosulfonyl, amino, $C_1$-$C_4$alkylamino, di($C_1$-$C_4$alkyl)amino, halogen, cyano, nitro, phenyl and/or by benzylthio; it being possible for phenyl and benzylthio in turn to be substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or by nitro, and substituents on the nitrogen in the heterocyclic ring are other than halogen;

$Ra_5$ is hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_6$alkylsulfonyloxy, hydroxy, mercapto, amino, $C_1$-$C_6$alkylamino, di($C_1$-$C_6$alkyl)amino, $C_1$-$C_4$alkylsulfonylamino, $C_1$-$C_4$alkylsulfonyl-N($C_1$-$C_4$alkyl)-, $C_1$-$C_6$alkylaminosulfonyl, di($C_1$-$C_6$alkyl)aminosulfonyl, cyano, halogen, $C_1$-$C_4$alkoxy-$C_1$-$C_4$alkyl, $C_1$-$C_4$alkylthio-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl, triazolyl, phenyl, phenylthio, phenylsulfinyl, phenylsulfonyl or phenoxy; it being possible for the phenyl-containing groups to be substituted by $C_1$-$C_3$alkyl, $C_1$-$C_3$haloalkyl, $C_1$-$C_3$alkoxy, $C_1$-$C_3$haloalkoxy, halogen, cyano or by nitro; and agronomically acceptable salts/N-oxides/isomers/enantiomers of those compounds.

The alkyl groups appearing in the above substituent definitions may be straight-chain or branched and are, for example, methyl, ethyl, n-propyl, isopropyl, n-butyl, sec-butyl, isobutyl or tert-butyl. Alkoxy, alkenyl and alkynyl radicals are derived from the mentioned alkyl groups. The alkenyl and alkynyl groups may be mono- or poly-unsaturated. Alkoxy is, for example, methoxy, ethoxy, propoxy, isopropoxy, n-butoxy, isobutoxy, sec-butoxy or tert-butoxy. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl.

Halogen is generally fluorine, chlorine, bromine or iodine. The same applies also to halogen in conjunction with other meanings, such as haloalkyl or halophenyl. Haloalkyl groups having a chain length of from 1 to 6 carbon atoms are, for example, fluoromethyl, difluoromethyl, chlorodifluoromethyl, trifluoromethyl, chloromethyl, dichloromethyl, trichloromethyl, 2,2,2-trifluoroethyl, 1-fluoroethyl, 2-fluoroethyl, 2-chloroethyl, 2-fluoroprop-2-yl, pentafluoroethyl, 1,1-difluoro-2,2,2-trichloroethyl, 2,2,3,3-tetrafluoroethyl and 2,2,2-trichloroethyl, pentafluoroethyl, heptafluoro-n-propyl and perfluoro-n-hexyl.

Alkenyl and alkynyl groups may be mono- or poly-unsaturated, so that alkyl, alkenyl and alkynyl chains having one or more double or triple bonds are also included. Alkenyl is, for example, vinyl, allyl, isobuten-3-yl, $CH_2$=CH—$CH_2$—CH=CH—, $CH_2$=CH—$CH_2$—$CH_2$—CH=CH— or $CH_3$—CH=CH—$CH_2$—CH=CH—. A preferred alkynyl is, for example, propargyl, and a preferred allenyl is $CH_2$=C=$CH_2$—.

An alkylene chain may also be substituted by one or more $C_1$-$C_3$alkyl groups, especially by methyl groups. Such alkylene chains and alkylene groups are preferably unsubstituted. The same applies also to all groups containing $C_3$-$C_6$cycloalkyl, $C_3$-$C_5$oxacycloalkyl, $C_3$-$C_5$thiacycloalkyl, $C_3$-$C_4$dioxacycloalkyl, $C_3$-$C_4$dithiacycloalkyl or $C_3$-$C_4$oxathiacycloalkyl which occur, for example, also as part of oxygen- and sulfur-containing heterocyclic ring systems of the radicals $Ra_1$ and $Ra_2$.

A $C_1$-$C_4$alkylene, $C_1$-$C_4$alkenylene or $C_2$-$C_4$alkynylene chain which may be interrupted by oxygen, —N($C_1$-$C_4$alkyl)-, sulfur, sulfinyl or by sulfonyl, or in $X_2$ or $X_6$ in the meaning of a $C_1$-$C_6$alkylene, $C_3$-$C_6$alkenylene or $C_3$-$C_6$alkynylene chain which may be mono- or poly-substituted by halogen or by $X_4$ or $X_8$, and wherein the unsaturated bonds of the chain are not bonded directly to the substituent $X_1$ or $X_5$, is to be understood as being, for example —$CH_2$—, —$CH_2CH_2$—, 13 $CH_2CH_2CH_2$—, —$CH_2CH_2CH_2CH_2$—, —CH($CH_3$)—, —$CH_2$CH($CH_3$)—, —$CH_2$CH($CH_3$)$CH_2$—, —$CH_2$CH(Cl)$CH_2$—, —$CH_2$CH(O$CH_3$)$CH_2$—, —$CH_2$O—, —O$CH_2$—, —$CH_2$O$CH_2$—, —O$CH_2CH_2$—, —O$CH_2CH_2CH_2$—, —$CH_2$O$CH_2CH_2$—, —$CH_2$OCH (CH₃)CH₂—, —SCH₂—, —SCH₂CH₂—, —SCH₂CH₂CH₂—, —CH₂S—, —CH₂SCH₂—, —CH₂S(O)CH₂—, —CH₂SO₂CH₂—, —CH₂SCH₂CH₂—, —CH₂S(O)CH₂CH₂—, —CH₂SO₂CH₂CH₂—, —CH₂SO₂NH—, —CH₂N(CH₃)SO₂CH₂CH₂—, —N(SO₂Me)CH₂CH₂—, —CH₂C(O)NH— or —CH₂NHC(O)CH₂—. A C₂-C₄alkenylene chain which may be interrupted by oxygen is accordingly to be understood as being, for example, —CH=CH—CH₂—, —CH=CH—CH₂CH₂— or —CH=CHCH₂OCH₂—; and a C₂-C₄alkynylene chain which may be interrupted by oxygen is to be understood as being, for example, —C≡C—, —C≡CCH₂—, —C≡CCH₂O—, —C≡CCH₂OCH₂— or —OC≡CCH₂—.

A three- to ten-membered mono- or bi-cyclic ring system Ra₁ or Ra₂, which may be interrupted once or up to three times selected from oxygen, sulfur, S(O), SO₂, N(Ra₆), carbonyl and C(=NORa₇) and which is bonded to the carbon atom of the substituent A₄ or to the group Q₁ or Q₂ either directly or by way of a C₁-C₄alkylene, C₁-C₄alkenylene or C₂-C₄alkynylene bridge which may be interrupted by oxygen, —N(C₁-C₄alkyl)-, sulfur, sulfinyl or by sulfonyl, is to be understood as being, for example, 1-methyl-1H-pyrazol-3-yl, 1-ethyl-1H-pyrazol-3-yl, 1-propyl-1H-pyrazol-3-yl, 1H-pyrazol-3-yl, 1,5-dimethyl-1H-pyrazol-3-yl, 4-chloro-1-methyl-1H-pyrazol-3-yl, 1H-pyrazol-1-yl, 3-methyl-1H-pyrazol-1-yl, 3,5-dimethyl-1H-pyrazol-1-yl, 3-isoxazolyl, 5-methyl-3-isoxazolyl, 3-methyl-5-isoxazolyl, 5-isoxazolyl, 1H-pyrrol-2-yl, 1-methyl-1H-pyrrol-2-yl, 1H-pyrrol-1-yl, 1-methyl-1H-pyrrol-3-yl, 2-furyl, 5-methyl-2-furyl, 3-furyl, 5-methyl-2-thienyl, 2-thienyl, 3-thienyl, 1-methyl-1H-imidazol-2-yl, 1H-imidazol-2-yl, 1-methyl-1H-imidazol-4-yl, 1-methyl-1H-imidazol-5-yl, 4-methyl-2-oxazolyl, 5-methyl-2-oxazolyl, 2-oxazolyl, 2-methyl-5-oxazolyl, 2-methyl-4-oxazolyl, 4-methyl-2-thiazolyl, 5-methyl-2-thiazolyl, 2-thiazolyl, 2-methyl-5-thiazolyl, 2-methyl-4-thiazolyl, 3-methyl-4-isothiazolyl, 3-methyl-5-isothiazolyl, 5-methyl-3-isothiazolyl, 1-methyl-1H-1,2,3-triazol-4-yl, 2-methyl-2H-1,2,3-triazol-4-yl, 4-methyl-2H-1,2,3-triazol-2-yl, 1-methyl-1H-1,2,4-triazol-3-yl, 1,5-dimethyl-1H-1,2,4-triazol-3-yl, 3-methyl-1H-1,2,4-triazol-1-yl, 5-methyl-1H-1,2,4-triazol-1-yl, 4,5-dimethyl-4H-1,2,4-triazol-3-yl, 4-methyl-4H-1,2,4-triazol-3-yl, 4H-1,2,4-triazol-4-yl, 5-methyl-1,2,3-oxadiazol-4-yl, 1,2,3-oxadiazol-4-yl, 3-methyl-1,2,4-oxadiazol-5-yl, 5-methyl-1,2,4-oxadiazol-3-yl, 4-methyl-3-furazanyl, 3-furazanyl, 5-methyl-1,2,4-oxadiazol-2-yl, 5-methyl-1,2,3-thiadiazol-4-yl, 1,2,3-thiadiazol-4-yl, 3-methyl-1,2,4-thiadiazol-5-yl, 5-methyl-1,2,4-thiadiazol-3-yl, 4-methyl-1,2,5-thiadiazol-3-yl, 5-methyl-1,3,4-thiadiazol-2-yl, 1-methyl-1H-tetrazol-5-yl, 1H-tetrazol-5-yl, 5-methyl-1H-tetrazol-1-yl, 2-methyl-2H-tetrazol-5-yl, 2-ethyl-2H-tetrazol-5-yl, 5-methyl-2H-tetrazol-2-yl, 2H-tetrazol-2-yl, 2-pyridyl, 6-methyl-2-pyridyl, 4-pyridyl, 3-pyridyl, 6-methyl-3-pyridazinyl, 5-methyl-3-pyridazinyl, 3-pyridazinyl, 4,6-dimethyl-2-pyrimidinyl, 4-methyl-2-pyrimidinyl, 2-pyrimidinyl, 2-methyl-4-pyrimidinyl, 2-chloro-4-pyrimidinyl, 2,6-dimethyl-4-pyrimidinyl, 4-pyrimidinyl, 2-methyl-5-pyrimidinyl, 6-methyl-2-pyrazinyl, 2-pyrazinyl, 4,6-dimethyl-1,3,5-triazin-2-yl, 4,6-dichloro-1,3,5-triazin-2-yl, 1,3,5-triazin-2-yl, 4-methyl-1,3,5-triazin-2-yl, 3-methyl-1,2,4-triazin-5-yl, 3-methyl-1,2,4-triazin-6-yl,

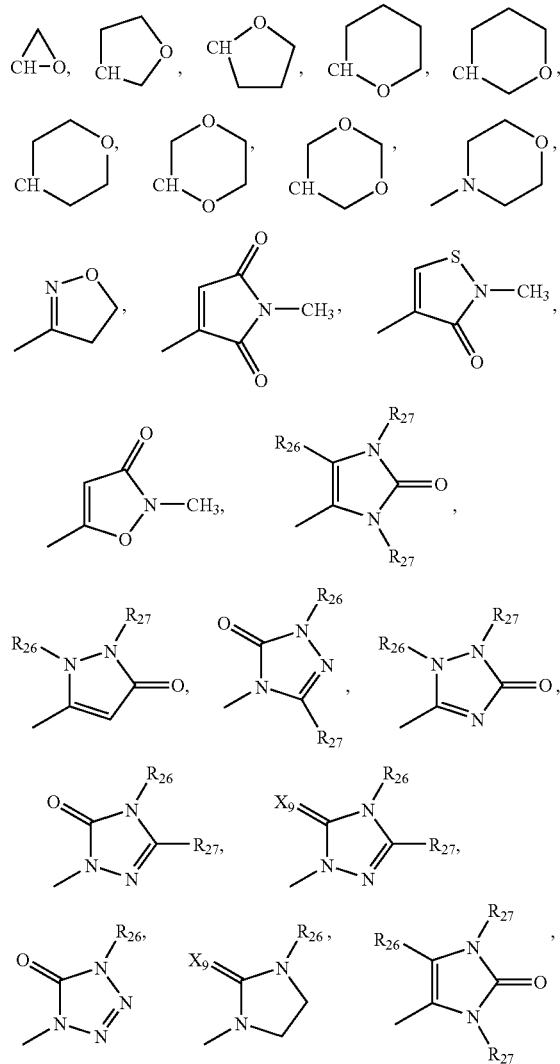

wherein each R₂₆ is methyl, each R₂₇ independently is hydrogen, C₁-C₃alkyl, C₁-C₃alkoxy, C₁-C₃alkylthio or trifluoromethyl, and X₉ is oxygen or sulfur.

A further annellated (fused-on), monocyclic or bicyclic ring system which is formed, for example, by two adjacent substituents Ra₁ and Ra₂ or Ra₁ and Ra₅ and which is interrupted once or up to three times selected from oxygen, sulfur, S(O), SO₂, —N(Ra₆)-, carbonyl and C(=NORa₇) and which may be additionally substituted by one or more substituents is to be understood as being, for example, an annellated, bidentate ring system of formula

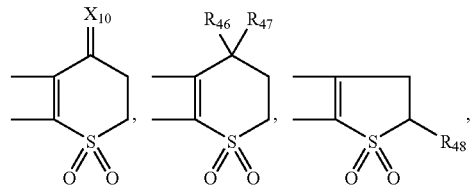

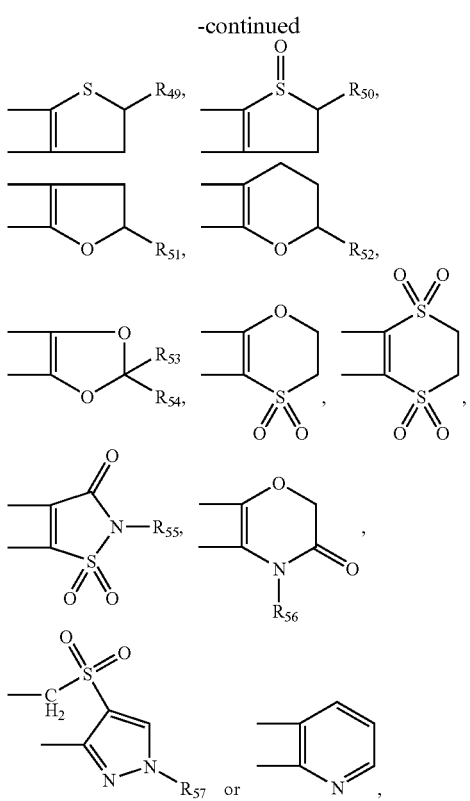

wherein especially R$_{46}$ is hydrogen, halogen, C$_1$-C$_4$alkyl, C$_1$-C$_4$haloalkyl, C$_1$-C$_4$alkoxy or C$_1$-C$_4$alkylthio; R$_{47}$ is hydrogen, halogen, C$_1$-C$_4$alkyl or C$_1$-C$_4$alkoxy; R$_{50}$, R$_{51}$, R$_{52}$, R$_{53}$, R$_{54}$, R$_{55}$, R$_{56}$, R$_{57}$, R$_{58}$ and R$_{59}$ are each independently of the others hydrogen or C$_1$-C$_4$alkyl; and X$_{10}$ is oxygen or NOR$_{59}$.

A heteroaryl group Y substituted at least in the ortho position is to be understood as being especially a 5- or 6-membered aromatic heteroaryl group as defined hereinbefore which is, in addition, substituted once or up to three times by substituents selected from the meanings of Ra$_1$, Ra$_2$, Ra$_3$ and Ra$_4$ and Ra$_5$ at the nitrogen and/or at the carbon atoms.

Using the process according to the invention it is possible, especially advantageously, to prepare the cyclohexanedione herbicides described in WO 00/15615, WO 00/37437, WO 01/66522 and WO 01/94339.

Compounds of formula I that are highly suitable for preparation using the process according to the invention are those wherein R$_1$ and R$_2$ are hydrogen;

Q is Q$_1$, wherein A$_4$ is CRa$_1$ or N—(O)$_p$;

p is 0;

Ra$_1$ is hydrogen, C$_1$-C$_6$alkyl, hydroxy, C$_1$-C$_6$alkoxy, C$_1$-C$_6$haloalkoxy, C$_3$-C$_6$alkenyloxy, C$_3$-C$_6$haloalkenyloxy, C$_3$-C$_6$alkynyloxy, C$_1$-C$_4$alkoxy-C$_1$-C$_2$alkoxy, C$_1$-C$_4$alkoxy-C$_1$-C$_2$alkoxy-C$_1$-C$_2$alkoxy, (C$_3$-C$_6$cycloalkyl)-C$_1$-C$_2$alkoxy, (1,3-dioxolan-2-yl)-C$_1$-C$_2$alkoxy, (tetrahydro-furan-2-yl)-C$_1$-C$_2$alkoxy, (tetrahydro-furan-3-yl)oxy, (oxetan-3-yl)oxy, (C$_3$-C$_6$cycloalkyl)oxy, C$_1$-C$_4$alkylsulfonyloxy, C$_1$-C$_4$alkylthio, C$_1$-C$_4$alkylsulfonyl, C$_1$-C$_4$alkylamino, di(C$_1$-C$_4$alkyl)amino, C$_1$-C$_2$alkoxyethylamino, C$_1$-C$_2$alkoxyethyl-(N-methyl)amino, morpholino, C$_1$-C$_4$alkylcarbonylaminoethoxy, C$_1$-C$_4$alkoxycarbonyl, hydroxymethyl, C$_1$-C$_6$alkoxymethyl, C$_1$-C$_6$haloalkoxymethyl, C$_3$-C$_6$alkenyloxymethyl, C$_3$-C$_6$haloalkenyloxymethyl, C$_3$-C$_6$alkynyloxymethyl, C$_1$-C$_4$alkoxy-C$_1$-C$_2$alkoxymethyl, (C$_3$-C$_6$cycloalkyl)methoxymethyl, (1,3-dioxolan-2-yl)-methoxymethyl, (tetrahydro-furan-2-yl)methoxymethyl, (tetrahydro-furan-3-yl)oxymethyl, (oxetan-3-yl)oxymethyl, (C$_3$-C$_6$cycloalkyl)oxymethyl, C$_1$-C$_4$alkylcarbonylamino-C$_1$-C$_2$alkoxy, C$_1$-C$_4$haloalkyl, cyano, halogen, phenyl or benzyloxy, it being possible for a phenyl-containing group in turn to be substituted by C$_1$-C$_3$alkyl, C$_1$-C$_3$haloalkyl, C$_1$-C$_3$alkoxy, C$_1$-C$_3$haloalkoxy, halogen, cyano or by nitro;

Ra$_2$ is C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_3$-C$_6$-cycloalkyl, halo- or C$_1$-C$_2$alkoxymethyl-substituted C$_3$-C$_6$cycloalkyl, C$_1$-C$_6$alkoxy, C$_3$-C$_6$-alkenyloxy, C$_3$-C$_6$alkynyloxy, C$_1$-C$_6$haloalkoxy, C$_3$-C$_6$haloalkenyloxy, C$_1$-C$_4$alkoxy-C$_1$-C$_4$-alkoxy, C$_1$-C$_4$alkylthio-C$_1$-C$_4$alkoxy, C$_1$-C$_4$alkylsulfinyl-C$_1$-C$_4$alkoxy, C$_1$-C$_4$alkylsulfonyl-C$_1$-C$_4$-alkoxy, C$_1$-C$_4$alkoxycarbonyl-C$_1$-C$_4$alkoxy, C$_1$-C$_6$alkylthio, C$_1$-C$_6$alkylsulfinyl, C$_1$-C$_6$alkylsulfonyl, C$_1$-C$_6$haloalkylthio, C$_1$-C$_6$haloalkylsulfinyl, C$_1$-C$_6$haloalkylsulfonyl, C$_1$-C$_6$alkylaminosulfonyl, di(C$_1$-C$_6$alkyl)aminosulfonyl, C$_1$-C$_4$alkylsulfonyloxy, C$_1$-C$_4$haloalkylsulfonyloxy, C$_1$-C$_4$alkylsulfonylamino, C$_1$-C$_4$alkylsulfonyl-N(C$_1$-C$_4$-alkyl), cyano, halogen, hydroxy-C$_1$-C$_4$-alkyl, C$_1$-C$_4$alkoxy-C$_1$-C$_4$alkyl, C$_1$-C$_4$alkylthio-C$_1$-C$_4$alkyl, C$_1$-C$_4$alkylsulfinyl-C$_1$-C$_4$alkyl, C$_1$-C$_4$alkylsulfonyl-C$_1$-C$_4$alkyl, cyano-C$_1$-C$_4$alkyl, C$_1$-C$_6$alkylcarbonyloxy-C$_1$-C$_4$alkyl, C$_1$-C$_4$alkoxycarbonyl-C$_1$-C$_4$alkyl, C$_1$-C$_4$alkoxycarbonyloxy-C$_1$-C$_4$alkyl, phenoxy-C$_1$-C$_4$alkyl, benzyloxy-C$_1$-C$_4$alkyl, benzoyloxy-C$_1$-C$_4$alkyl, benzyloxy, benzylthio, phenoxy or phenylthio, it being possible for the phenyl-containing groups in turn to be substituted by C$_1$-C$_3$alkyl, C$_1$-C$_3$haloalkyl, C$_1$-C$_3$alkoxy, C$_1$-C$_3$haloalkoxy, halogen, cyano or by nitro; or Ra$_2$ is the group —X$_1$-X$_3$ or the group —X$_2$-X$_1$-X$_3$, wherein X$_1$, X$_2$ and X$_3$ are as defined hereinbefore; or Ra$_3$ is hydrogen; or Ra$_4$ is hydrogen or methyl; or Ra$_5$ is C$_1$-C$_6$haloalkyl, C$_2$-C$_6$haloalkenyl, C$_1$-C$_6$alkoxy, C$_1$-C$_6$haloalkoxy, C$_1$-C$_6$alkylthio, C$_1$-C$_6$alkylsulfinyl, C$_1$-C$_6$alkylsulfonyl, C$_1$-C$_6$haloalkylthio, C$_1$-C$_6$haloalkylsulfinyl, C$_1$-C$_6$haloalkylsulfonyl, C$_1$-C$_6$alkylsulfonyloxy, C$_1$-C$_4$alkylaminosulfonyl, di(C$_1$-C$_4$-alkyl)aminosulfonyl, C$_1$-C$_4$alkylsulfonylamino, C$_1$-C$_4$alkylsulfonyl-N(C$_1$-C$_4$alkyl)-, cyano, halogen, C$_1$-C$_4$alkoxymethyl, C$_1$-C$_4$alkylthiomethyl, C$_1$-C$_4$alkylsulfinylmethyl, C$_1$-C$_4$alkylsulfonylmethyl or 1H-1,2,4-triazol-1-yl.

Compounds of formula I that are especially highly suitable for preparation using the process according to the invention are those wherein R$_2$ and R$_5$ together are ethylene; (VI), R$_1$ and R$_6$ are hydrogen;

A$_2$ is C(R$_3$R$_4$)$_n$, wherein R$_3$ and R$_4$ are hydrogen and n is 1.

Reaction Step a):

Suitable bromine and chlorine sources are bromine, chlorine, their succinimides such as N-bromosuccinimide (NBS), bromo- and chloro-acetamides and alkyl hypohalites. A preferred bromine source is bromine or NBS, and a preferred chlorine source is chlorine. In the case of bromination it is advantageous for the HBr that is formed to be removed from the reaction mixture, which may be accomplished, for example, by introducing an inert gas such as, for example, argon or nitrogen, beneath the surface of the reaction mixture. Incorporation of the halogens into the reaction mixture can be carried out by dropwise addition or direct introduction beneath the surface of the reaction mixture. In the case of direct introduction, the halogens can be diluted with an inert gas such as, for example, argon or nitrogen.

The reaction according to Reaction Step a) is preferably carried out in the presence of a free-radical initiator such as, for example, benzoyl peroxide or azoisobutyronitrile. Illumination of the reaction mixture is, moreover, advantageous. The halogenation is preferably carried out in the presence of azoisobutyronitrile.

The reaction is preferably carried out in the presence of a solvent. Suitable solvents are chlorobenzene, hexane, acetonitrile, tetrahydrofuran, methylcyclohexane or CCl$_4$ and also mixtures thereof; special preference is given to chlorobenzene or CCl$_4$.

The temperatures are generally from 0° C. to 150° C.; preference is given to a range from 80° C. to 130° C.

Compounds of formula II are known; they are commercially available in some cases or can be prepared by known methods.

The compounds of formula III

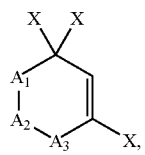

(III)

wherein $A_1$, $A_2$ and $A_3$ are as defined for formula I and X is either chlorine or bromine, are novel and were developed specifically for the process according to the invention, and the present invention accordingly also relates thereto. An especially valuable intermediate is the compound of formula IIIb

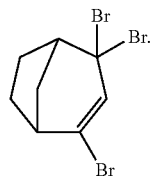

(IIIb)

Reaction Step b):

Reaction Step b) is preferably carried out with acid- or base-catalysis, preferably acid-catalysis. Suitable acids are mineral acids such as sulfuric acid, hydrochloric acid or bromic acid or organic acids such as acetic acid. Special preference is given to sulfuric acid. As bases there may be used organic or inorganic bases such as, for example, quaternary ammonium hydroxides or sodium hydroxide. For complete conversion at least 2 equivalents of water are used. In a preferred embodiment, first one equivalent of water is added to the compound of formula III until the monoketone of formula IV

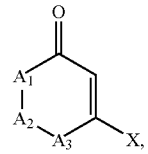

(IV)

wherein $A_1$, $A_2$ and $A_3$ are as defined hereinbefore and X is chlorine or bromine, is formed and then, as a result of the addition of the second equivalent of water, the diketone of formula I is formed. The selectivity of the reaction can be further increased using this preferred embodiment.

Reaction Step c):

Reaction Step c) is carried out in the absence of water and in the presence of a base, for example a tertiary amine, preferably triethylamine or diisopropylethylamine. The reaction is preferably carried out in the presence of a solvent such as a hydrocarbon, acetonitrile, ether or dipolar aprotic solvent, preferably in the presence of acetonitrile, toluene, xylene or chlorobenzene, at temperatures of from 80° C. to 130° C.

Reaction Step d):

In an especially preferred embodiment of the process according to the invention, the reaction according to Reaction Step d) is carried out without isolation of intermediates, that is to say the compound of formula VI obtained according to Reaction Step c) is treated in situ with cyanide ions in the presence of a base.

The cyanide ions are preferably used in amounts of from 0.01% to 15%. The reaction is preferably carried out at a temperature of from 50° C. to 150° C., especially at from 50° C. to 100° C., in the absence of water and in the presence of a base, for example from 0.1 to 2.5 equivalents of triethylamine, or Hünig's base.

A suitable cyanide ion source is, for example, sodium cyanide, potassium cyanide, copper(I) cyanide, acetone cyanohydrin or trimethylsilyl cyanide, preferably potassium cyanide. Suitable solvents for Reaction Step c) are, for example, hydrocarbons, acetonitriles, ethers, chlorinated hydrocarbons and dipolar aprotic solvents. Such enol ester rearrangements are described, for example, in EP-A-0 186 117.

In a preferred embodiment of the process according to the invention, some reaction steps are carried out in the form of a one-pot reaction. Very special preference is given to carrying out Reaction Steps c) and d) in the form of a one-pot reaction. It can also be advantageous to carry out the entire reaction (Reaction Steps a), b), c) and d)) in the form of a one-pot reaction, without isolation of intermediates. The possibility of carrying out the process according to the invention in a one-pot reaction constitutes a considerable advantage especially for large-scale application.

The process according to the invention will be explained in greater detail in the following Preparation Examples:

EXAMPLE P1

Preparation of 2,4,4-tribromo-bicyclo[3.2.1]oct-2-ene

To a solution of 15 g (88.9 mmol) of bicyclo[3.2.1]oct-2-ene in 250 ml of CCl$_4$ there are added, under a nitrogen atmosphere, 1.54 g (9.26 mmol) of azoisobutyronitrile. The reaction mixture is then illuminated with a strong lamp and heated to a temperature of 80° C., with stirring. 30 g (0.17 mol) of N-bromosuccinimide (NBS) are then added and stirring is carried out for 1.25 hours at a temperature of 80° C. Then, at intervals of about 1.5 hours, three further portions of 30 g (0.17 mol), 11.6 g (64.5 mmol) and 18.4 g (0.1 mol) of NBS are added and the reaction mixture is maintained at that temperature, with stirring, until conversion is complete. The reaction mixture is then cooled to ambient temperature and diluted with 100 ml of isohexane. After filtration and removal of the solvent in vacuo, 43.2 g (52% of theory) of 2,4,4-tribromo-bicyclo[3.2.1]oct-2-ene are obtained as a red-brown oil.

MS: 265 ($M^+$-Br), 237, 183, 156, 119, 105, 89, 77, 63, 51, 39.

$^1$H NMR (CDCl$_3$): 1.55-1.65 (m, 1H), 1.85-2.20 (m, 4H), 2.55-2.60 (d, 1H), 2.70-2.80 (d, 1H), 3.20 (d, 1H), 6.35 (s, 1H).

EXAMPLE P2

Preparation of 4-bromo-bicyclo[3.2.1]oct-3-en-2-one

To a solution of 89.9 g (7.9% w/w, 100%=7.1 g, 20.6 mmol) of 2,4,4-tribromobicyclo[3.2.1]oct-2-ene in chlorobenzene there are added 100 ml of acetonitrile and 100 ml of 10% sulfuric acid and stirring is carried out for 50 minutes at ambient temperature. The pH is then adjusted to 7 using aqueous sodium hydroxide solution and the aqueous phase is separated off. The organic phase is washed with 50 ml of water and then dried using magnesium sulfate. After filtration and removal of the acetonitrile using a rotary evaporator, 57.8 g (88% of theory) of 4-bromo-bicyclo[3.2.1]oct-3-en-2-one are obtained as a 6.3% solution in chlorobenzene.

MS: 200($M^+$), 172, 159, 146, 131, 121, 91, 77, 65, 51, 39.

$^1$H NMR (CDCl$_3$): 1.60-1.70 (m, 2H), 1.85-1.95 (m, 1H), 1.95-2.10 (m, 1H), 2.10-2.25 (m, 2H), 2.95 (t, 1H), 3.20 (t, 1H), 6.20 (s, 1H).

EXAMPLE P3

Preparation of 3-(2-nitro-4-methylsulfonyl-phenyl-carbonyloxy)-cyclohex-2-en-1-one

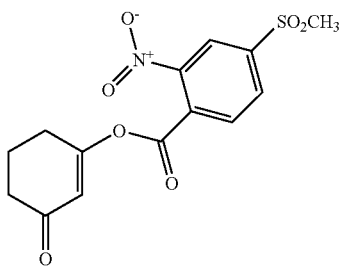

To a mixture of 157 mg (1.15 mmol) of 3-chlorocyclohex-2-en-1-one (prepared as described in Synthesis (1974), (1), 47-8), 16 mg (0.12 mmol) of ZnCl$_2$, 297 mg (1.15 mmol) of 2-nitro-4-methylsulfonylbenzoic acid and 3 ml of anhydrous acetonitrile there are added dropwise, under a nitrogen atmosphere, over the course of 15 minutes, 166 mg (1.27 mmol) of diisopropylethylamine. A further 2 ml of acetonitrile are then added and the reaction mixture is maintained at a temperature of 45° C. for 18 hours in an oil bath, with stirring. The reaction mixture is then heated up again and maintained at reflux temperature for 40 hours. The reaction mixture is then brought to ambient temperature and the solvent is removed in vacuo. 25 ml of dichloromethane and 0.35 g of 36% hydrochloric acid in 5 ml of water are then added and the phases are separated. The organic phase is washed twice with 10 ml of water, dried using magnesium sulfate and concentrated in vacuo. 197 mg of 3-(2-nitro-4-methylsulfonyl-phenylcarbonyloxy)-cyclohex-2-en-1-one are obtained in the form of a brown oil.

$^1$H NMR (CDCl$_3$): 2.10-2.20 (m, 2H), 2.45-2.50 (m, 2H), 2.70-2.75 (m, 2H), 3.20 (s, 3H, C$\underline{H}_3$SO$_2$), 6.10 (s, 1H, C=C$\underline{H}$), 8.00 (d, 1H, ar. $\underline{H}$), 8.35 (d, 1H, ar. $\underline{H}$), 8.65 (s, 1H, ar. $\underline{H}$).

EXAMPLE P4

Preparation of 3-(2-methoxyethoxymethyl-6-trifluoromethyl-pyridin-3-ylcarbonyloxy)-cyclohex-2-en-1-one

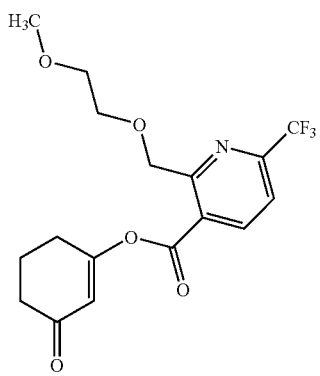

To a mixture of 157 mg (1.15 mmol) of 3-chlorocyclohex-2-en-1-one, 16 mg (0.12 mmol) of ZnCl$_2$, 324 mg (1.15 mmol) of 2-methoxyethoxymethyl-6-trifluoromethylnicotinic acid (preparation described in WO 2001094339) and 2 ml of toluene there are added dropwise, under a nitrogen atmosphere, over the course of 15 minutes, 166 mg (1.27 mmol) of diisopropylethylamine. A further 2 ml of toluene are then added and the reaction mixture is maintained under moderate reflux for 18 hours in an oil bath, with stirring. The reaction mixture is then brought to ambient temperature and 30 ml of dichloromethane and 20 ml of water are added. The organic phase is separated off and washed twice with 0.1M hydrochloric acid (20 ml) and twice with water (10 ml). After drying using magnesium sulfate and concentrating in vacuo, 226 mg of 3-(2-methoxyethoxymethyl-6-trifluoromethyl-pyridin-3-ylcarbonyloxy)-cyclohex-2-en-1-one are obtained in the form of an orange-brown oil.

MS: 373 ($M^+$), 354, 328, 262, 230, 202, 187, 159, 139, 109, 95, 59, 45.

$^1$H NMR (CDCl$_3$): 2.10-2.20 (m, 2H), 2.45-2.50 (m, 2H), 2.70-2.75 (m, 2H), 3.35 (s, 3H, C$\underline{H}_3$O), 3.50 (CH$_2$C$\underline{H}_2$O), 3.70 (OC$\underline{H}_2$CH$_2$), 5.00 (s, 2H, arC$\underline{H}_2$), 6.10 (s, 1H, C=C$\underline{H}$), 7.75 (d, 1H, ar. $\underline{H}$), 8.30 (d, 1H, ar. $\underline{H}$).

EXAMPLE P5

Preparation of 4-(2-methoxyethoxymethyl-6-trifluoromethyl-pyridin-3-ylcarbonyloxy)-bicyclo[3.2.1]oct-3-en-2-one

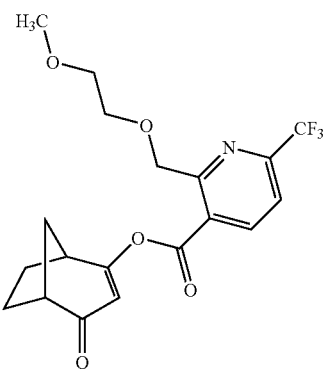

A mixture of 200 mg (1.15 mmol) of 4-chlorobicyclo[3.2.1]oct-3-en-2-one, 16 mg (0.12 mmol) of $ZnCl_2$, 324 mg (1.15 mmol) of 2-methoxyethoxymethyl-6-trifluoromethylnicotinic acid, 166 mg (1.27 mmol) of diisopropylethylamine and 5 ml of toluene is stirred at room temperature under a nitrogen atmosphere until a clear brown solution having a white sediment is formed. With stirring, the reaction mixture is then maintained under moderate reflux for 26 hours in an oil bath. The reaction mixture is then cooled to ambient temperature and 30 ml of dichloromethane are added. The solution is then washed twice with water (20 ml each time), then twice with 0.1M hydrochloric acid (20 ml each time) and again twice with water (15 ml each time). After drying the organic solution using magnesium sulfate and concentrating in vacuum, 284 mg of 4-(2-methoxyethoxymethyl-6-trifluoromethyl-pyridin-3-ylcarbonyloxy)-bicyclo[3.2.1]oct-3-en-2-one are obtained in the form of a brown oil.

MS: 399 ($M^+$), 380, 354, 262, 230, 204, 187, 159, 139, 121, 91.

$^1$H NMR ($CDCl_3$): 1.65-1.75 (m, 2H), 2.05-2.30 (m, 4H), 3.00 (br t, 1H), 3.10 (br s, 1H), 3.35 (s, 3H, OC$\underline{H}_3$), 3.50 (m, 2H, C$\underline{H}_2$C$\underline{H}_2$O), 3.70 (m, 2H, OC$\underline{H}_2$C$\underline{H}_2$), 5.00 (s, 2H, ar. C$\underline{H}_2$), 5.90 (s, 1H. C=C$\underline{H}$), 7.75 (d, 1H. ar. $\underline{H}$), 8.30 (d, 1H. ar. $\underline{H}$).

EXAMPLE P6

Preparation of 4-(4-chlorophenyl-carbonyloxy)-bicyclo[3.2.1]oct-3-en-2-one

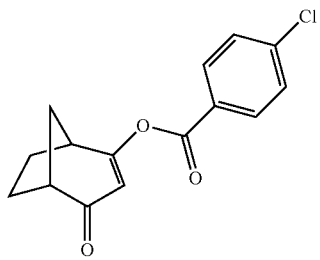

A mixture of 500 mg of 4-chlorobicyclo[3.2.1]oct-3-en-2-one, 440 mg of $ZnCl_2$, 400 mg of 4-chlorobenzoic acid, 1.05 g of diisopropylethylamine and 5 ml of toluene is stirred at room temperature under a nitrogen atmosphere at reflux temperature for 6 hours. After cooling, the reaction mixture is then diluted with dichloromethane and washed with 5% aqueous sulfuric acid and 5% aqueous sodium hydroxide. After concentration of the organic phase to dryness by evaporation, 0.6 g of 4-(4-chlorophenyl-carbonyloxy)-bicyclo[3.2.1]oct-3-en-2-one is obtained.

$^1$H NMR ($CDCl_3$): 1.65-1.8 (m, 2H), 2.0-2.4 (m, 4H), 2.95-3.1 (m, 2H, bridgehead), 5.85 (s, 1H, vinyl), 6.95-7.05 (m, 2H, aryl), 8.0-8.1 (m, 2H, aryl).

EXAMPLE P7

Preparation of 4-phenyl-carbonyloxy-bicyclo[3.2.1]oct-3-en-2-one

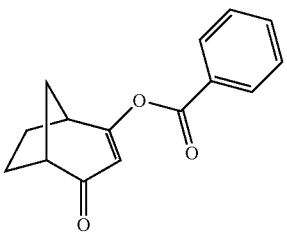

A mixture of 500 mg of 4-chlorobicyclo[3.2.1]oct-3-en-2-one, 440 mg of $ZnCl_2$, 400 mg of 4-benzoic acid, 1.05 g of diisopropylethylamine and 5 ml of toluene is stirred at room temperature under a nitrogen atmosphere at reflux temperature for 8 hours. After cooling, the reaction mixture is then diluted with dichloromethane and washed with 10% aqueous sulfuric acid. After concentration of the organic phase to dryness by evaporation, 0.4 g of 4-phenyl-carbonyloxy-bicyclo[3.2.1]oct-3-en-2-one is obtained.

$^1$H NMR ($CDCl_3$): 1.65-1.8 (m, 2H), 2.0-2.4 (m, 4H), 2.95-3.1 (m, 2H, bridgehead), 5.85 (s, 1H, vinyl), 6.95-7.05 (m, 2H, aryl), 7.1-7.2 (m, 1H, aryl), 8.05-8.15 (m, 2H, aryl).

EXAMPLE P8

Preparation of 4-(2-methoxyethoxymethyl-6-trifluoromethyl-pyridin-3-ylcarbonyloxy)-bicyclo[3.2.1]oct-3-en-2-one

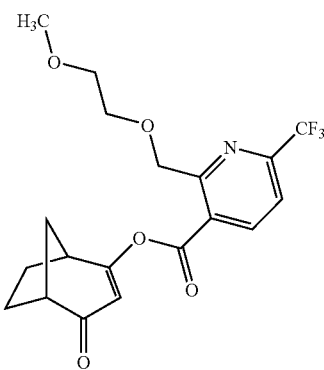

A mixture of 27 g of a 6.2% solution of 4-bromobicyclo[3.2.1]oct-3-en-2-one in chlorobenzene, 110 mg of $ZnCl_2$, 2.34 g of 2-methoxyethoxymethyl-6-trifluoromethylnicotinic acid and 1.2 g of Hünig's base is stirred at room temperature under a nitrogen atmosphere until a dark-brown solution is formed. With stirring, the reaction mixture is then maintained under moderate reflux for 19 hours in an oil bath. The mixture is then divided into 2 portions. To one portion there are added a further 1.12 g of 2-methoxyethoxymethyl-6-trifluoromethylnicotinic acid, 0.06 g of $ZnCl_2$ and 0.6 g of Hünig's base. With stirring, the reaction mixture is then maintained under moderate reflux for 12 hours in an oil bath. The solution is then washed twice with 0.1M hydrochloric acid (20 ml each time) and twice with water (20 ml each time). After drying the organic solution using magnesium sulfate and concentrating in vacuo, 3.9 g of 4-(2-methoxyethoxymethyl-6-trifluoromethyl-pyridin-3-ylcarbonyloxy)-bicyclo[3.2.1]oct-3-en-2-one are obtained in the form of a brown oil.

MS: 399 ($M^+$), 380, 354, 262, 230, 202, 187, 159, 139, 121, 91.

$^1$H NMR ($CDCl_3$): 1.65-1.75 (m, 2H), 2.05-2.30 (m, 4H), 3.00 (br t, 1H), 3.10 (br s, 1H), 3.35 (s, 3H, O$\underline{C}H_3$), 3.50 (m, 2H, $CH_2\underline{C}H_2O$), 3.70 (m, 2H, O$\underline{C}H_2CH_2$), 5.00 (s, 2H, ar. C$\underline{H}_2$), 5.90 (s, 1H, C=C$\underline{H}$), 7.75 (d, 1H, ar. $\underline{H}$), 8.30 (d, 1H, ar. $\underline{H}$).

EXAMPLE P9

Preparation of 4-hydroxy-3-(2-methoxyethoxymethyl-6-trifluoromethyl-pyridin-3-ylcarbonyl)-bicyclo[3.2.1]oct-3-en-2-one

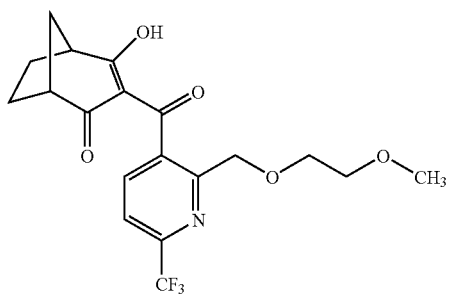

To a mixture of 200 mg (1.15 mmol) of 4-chlorobicyclo[3.2.1]oct-3-en-2-one, 16 mg (0.12 mmol) of $ZnCl_2$, 324 mg (1.15 mmol) of 2-methoxyethoxymethyl-6-trifluoromethylnicotinic acid and 2 ml of toluene there are added dropwise, under a nitrogen atmosphere, over the course of 15 minutes, 166 mg (1.27 mmol) of diisopropylethylamine. A further 2 ml of toluene are then added and the reaction mixture is maintained under moderate reflux for 23 hours in an oil bath, with stirring. The reaction mixture is then cooled to ambient temperature, and 4 ml of acetonitrile, 2 drops of cyanohydrin, 465 mg of triethylamine and a further 1 ml of acetonitrile are added. After drying the organic phase using magnesium sulfate and concentrating in vacuo, 452 mg of 4-hydroxy-3-(2-methoxyethoxymethyl-6-trifluoromethyl-pyridin-3-ylcarbonyl)-bicyclo[3.2.1]oct-3-en-2-one are obtained in the form of a viscous oil.

MS: 399 ($M^+$), 380, 356, 340, 310, 282, 256, 228, 202, 174, 152, 128, 67, 45.

$^1$H NMR ($CDCl_3$): 1.70-1.80 (m, 2H), 2.05-2.30 (m, 4H), 2.90 (br s, 1H), 3.15 (br s, 1H), 3.30 (s, 3H, O$\underline{C}H_3$), 3.40 (m, 2H, $CH_2\underline{C}H_2O$), 3.50 (m, 2H, O$\underline{C}H_2CH_2$), 4.75 (s, 2H, ar. C$\underline{H}_2$), 7.60 (s, 2H, ar. $\underline{H}$).

What is claimed is:
1. A process for the preparation of a compound of formula I

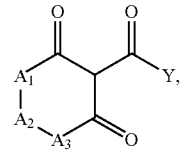

wherein Y is an organic substituent which is so selected that the compound of formula I has a pK value of from 1 to 5;

$A_1$ is $CR_1R_2$;

$A_2$ is oxygen, C(O), $SO_2$ or $(CR_3R_4)_n$;

n is 1 or 2;

$A_3$ is $CR_5R_6$;

$R_1$, $R_2$, $R_3$, $R_4$, $R_5$ and $R_6$ are each independently of the others $C_1$-$C_4$alkyl which may be mono-, di- or tri-substituted by $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl or by heteroaryl, it being possible for the phenyl and heteroaryl groups in turn to be mono-, di- or tri-substituted by $C_1$-$C_4$alkoxy, halogen, hydroxy, cyano, hydroxycarbonyl, $C_1$-$C_4$alkoxycarbonyl, $C_1$-$C_4$alkylsulfonyl or by $C_1$-$C_4$haloalkyl, the substituents on the nitrogen in the heterocyclic ring being other than halogen; and/or $R_1$, $R_2$, $R_3$, $R_4$, $R_5$ and $R_6$ are each independently of the others hydrogen, $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl or heteroaryl, it being possible for the phenyl and heteroaryl groups in turn to be mono-, di- or tri-substituted by $C_1$-$C_4$alkoxy, halogen, hydroxy, cyano, hydroxycarbonyl, $C_1$-$C_4$alkoxycarbonyl, $C_1$-$C_4$alkylsulfonyl or by $C_1$-$C_4$haloalkyl, the substituents on the nitrogen in the heterocyclic ring being other than halogen; and/or $R_1$ and $R_2$ together form a 3- to 5-membered carbocyclic ring which may be substituted by $C_1$-$C_4$alkyl and/or interrupted by oxygen, sulfur, S(O), $SO_2$, OC(O), $NR_7$ or by C(O); and/or $R_2$ and $R_4$ together or $R_2$ and $R_5$ together form a $C_1$-$C_3$alkylene chain which may be interrupted by oxygen, sulfur, SO, $SO_2$, OC(O), $NR_8$ or by C(O); it being possible for that $C_1$-$C_3$alkylene chain in turn to be substituted by $C_1$-$C_4$alkyl; and $R_7$ and $R_8$ are each independently of the other $C_1$-$C_4$alkyl, $C_1$-$C_4$haloalkyl, $C_1$-$C_4$alkylsulfonyl, $C_1$-$C_4$alkylcarbonyl or $C_1$-$C_4$alkoxycarbonyl; in which process a) a compound of formula II

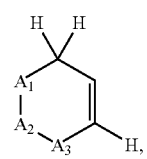

wherein $A_1$, $A_2$ and $A_3$ are as defined for formula I, is reacted with a bromine or chlorine source to form a compound of formula III

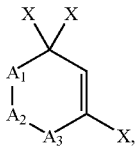

(III)

wherein $A_1$, $A_2$ and $A_3$ are as defined for formula I and X is chlorine or bromine;
b) that compound is reacted with water to form the compound of formula IV

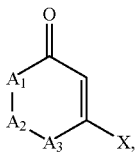

(IV)

wherein $A_1$, $A_2$ and $A_3$ are as defined for formula I and X is chlorine or bromine;
c) that compound is converted, using a compound of formula V $$M^+\text{-}O^-\text{—}C(O)\text{—}Y, \qquad (V)$$

wherein Y is as defined hereinbefore and $M^+$ is the hydrogen cation or an alkali metal ion, alkaline earth metal ion or ammonium ion, into the compound of formula VI

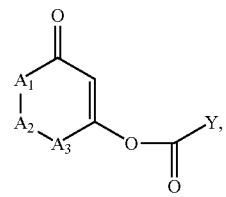

(VI)

wherein $A_1$, $A_2$, $A_3$ and Y are as defined for formula I, and
d) then that compound is treated with a cyanide source in the presence of a base.

* * * * *